United States Patent
Kim et al.

(10) Patent No.: US 10,761,025 B2
(45) Date of Patent: Sep. 1, 2020

(54) METHOD FOR DETECTING BIOMATERIAL USING LINEAR UPCONVERSION FLUORESCENT PROPERTY

(71) Applicants: Bionano Health Guard Research Center, Yuseong-gu, Daejeon (KR); Korea Institute of Science and Technology, Seongbuk-gu, Seoul (KR)

(72) Inventors: Sehoon Kim, Seoul (KR); Bong Hyun Chung, Seoul (KR); Youngsun Kim, Seoul (KR); Kyung Mi Park, Daejeon (KR); Young Hun Seo, Seoul (KR)

(73) Assignees: BIONANO HEALTH GUARD RESEARCH CENTER, Daejeon (KR); KOREA INSTITUTE OF SCIENCE AND TECHNOLOGY, Seoul (KR)

( * ) Notice: Subject to any disclaimer, the term of this patent is extended or adjusted under 35 U.S.C. 154(b) by 177 days.

(21) Appl. No.: 15/574,392

(22) PCT Filed: May 16, 2016

(86) PCT No.: PCT/KR2016/005166
§ 371 (c)(1),
(2) Date: Mar. 16, 2018

(87) PCT Pub. No.: WO2016/186412
PCT Pub. Date: Nov. 24, 2016

(65) Prior Publication Data
US 2018/0292317 A1    Oct. 11, 2018

(30) Foreign Application Priority Data
May 15, 2015   (KR) .................. 10-2015-0067872
May 16, 2016   (KR) .................. 10-2016-0059525

(51) Int. Cl.
*G01N 21/64* (2006.01)
*G01N 33/58* (2006.01)

(52) U.S. Cl.
CPC ....... *G01N 21/6428* (2013.01); *G01N 33/582* (2013.01); *G01N 2021/6439* (2013.01)

(58) Field of Classification Search
CPC ............ G01N 33/582; G01N 21/6428; G01N 2021/6439
See application file for complete search history.

(56) References Cited

U.S. PATENT DOCUMENTS

2009/0211345 A1    8/2009   Nahm et al.

OTHER PUBLICATIONS

Kaur et al., "Diketopyrrolopyrrole: Brilliant Red Pigment Dye-Based Fluorescent Probes and Their Applications," Chem. Soc. Rev., vol. 44, pp. 58-77 (Sep. 2014).
International Search Report dated Sep. 5, 2016 in Int'l Application No. PCT/KR2016/005166.
Liu et al., "C—H Activation: Making Diketopyrrolopyrrole Derivatives Easily Accessible," Journal of Materials Chemistry A, vol. 1, pp. 2795-2805 (2013).
Lunák et al., "Absorption and Fluorescence of Soluble Polar Diketo-Pyrrolo-Pyrroles," Dyes and Pigments, vol. 91, pp. 269-278 (2011).
Ftouni et al., "Functionalized Two-Photon Absorbing Diketopyrrolopyrrole-Based Fluorophores for Living Cells Fluorescent Microscopy," Bioconjugate Chemistry, vol. 24, pp. 942-950 (2013).

*Primary Examiner* — Shafiqul Haq
(74) *Attorney, Agent, or Firm* — Panitch Schwarze Belisario & Nadel LLP

(57) ABSTRACT

A method for detecting biomaterial by means of a dye having a linear upconversion fluorescent property is provided. The method includes the steps of: i) preparing a fluorophore having a linear upconversion fluorescent property; ii) reacting the fluorophore and biomaterial to obtain a reaction complex thereof; iii) exciting the reaction complex by means of a light source having a longer wavelength than the maximum light-emitting wavelength of the fluorophore; and iv) detecting and measuring the light-emitting signal having a shorter wavelength than the wavelength of the excited light emitted from the excited reaction complex. A system and a kit for detecting biomaterial using a dye having a linear upconversion fluorescent property are also provided.

8 Claims, 9 Drawing Sheets

[FIG. 1]
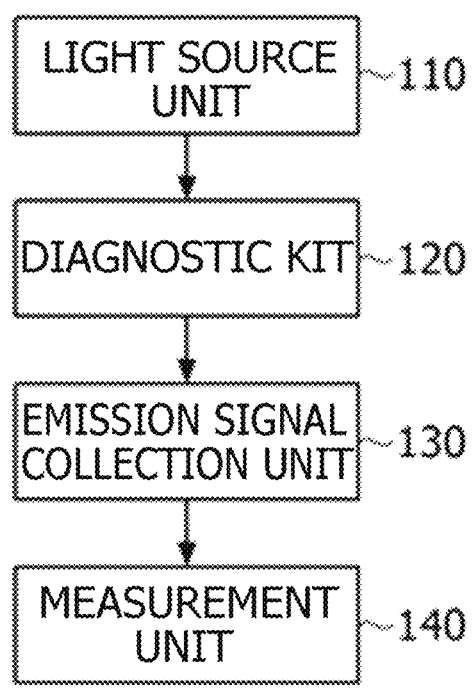

[Fig. 2A]
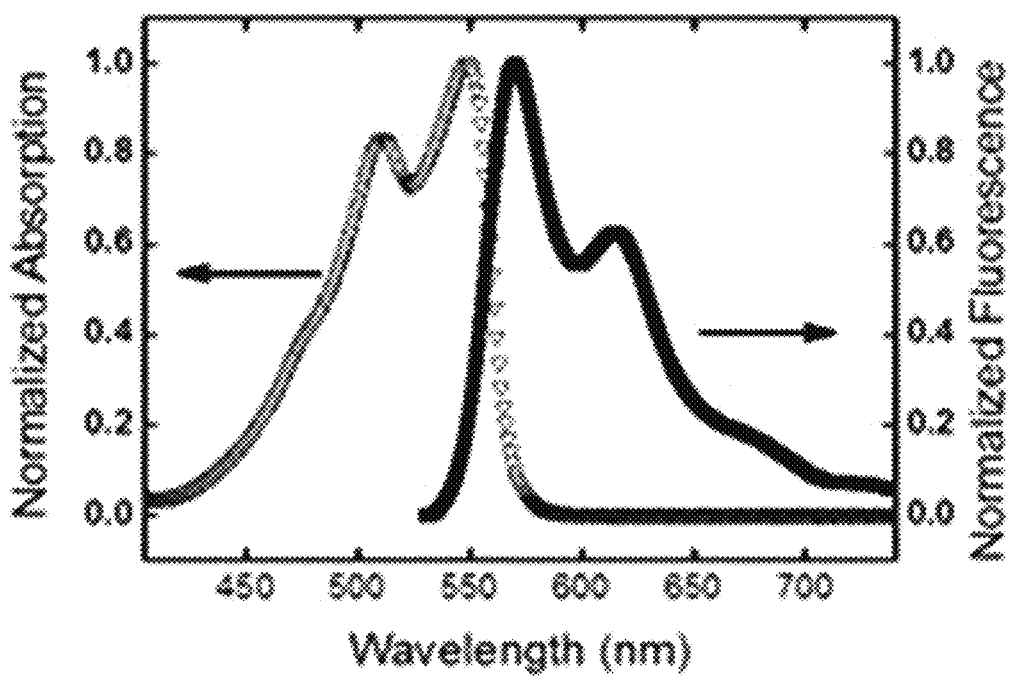
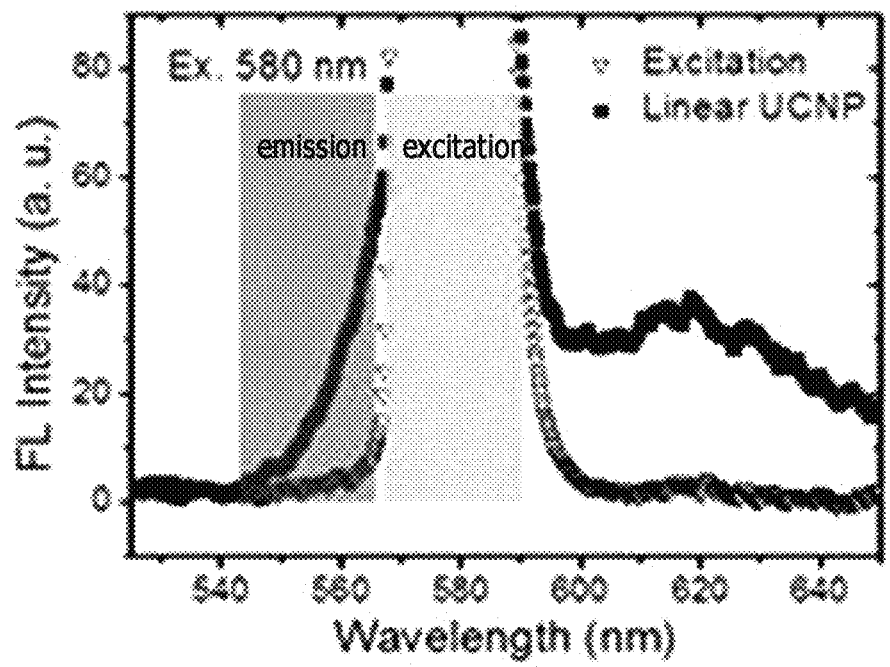
[Fig. 2B]

[FIG. 3]
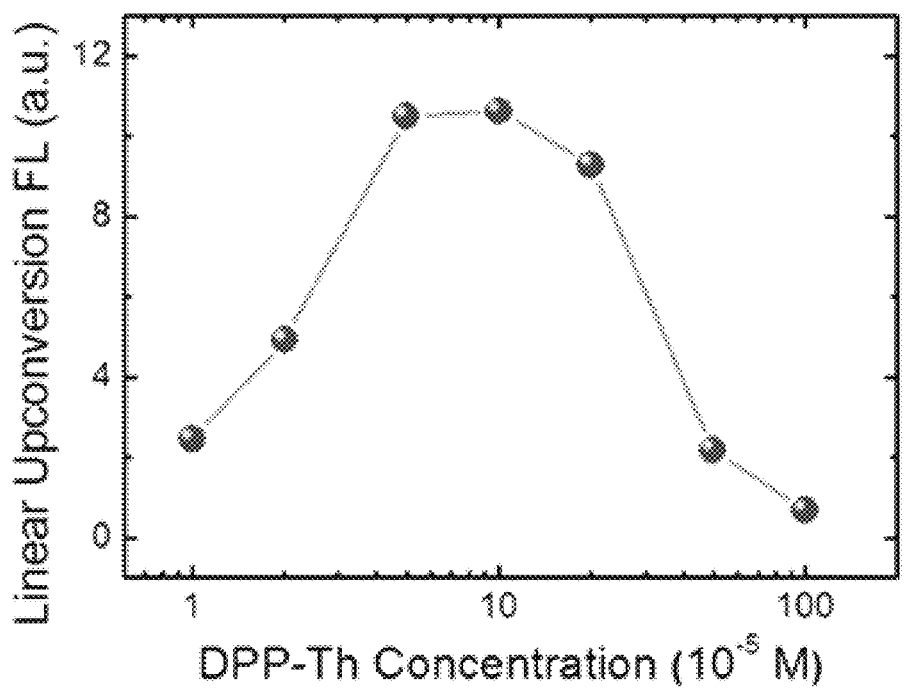
[FIG. 4]
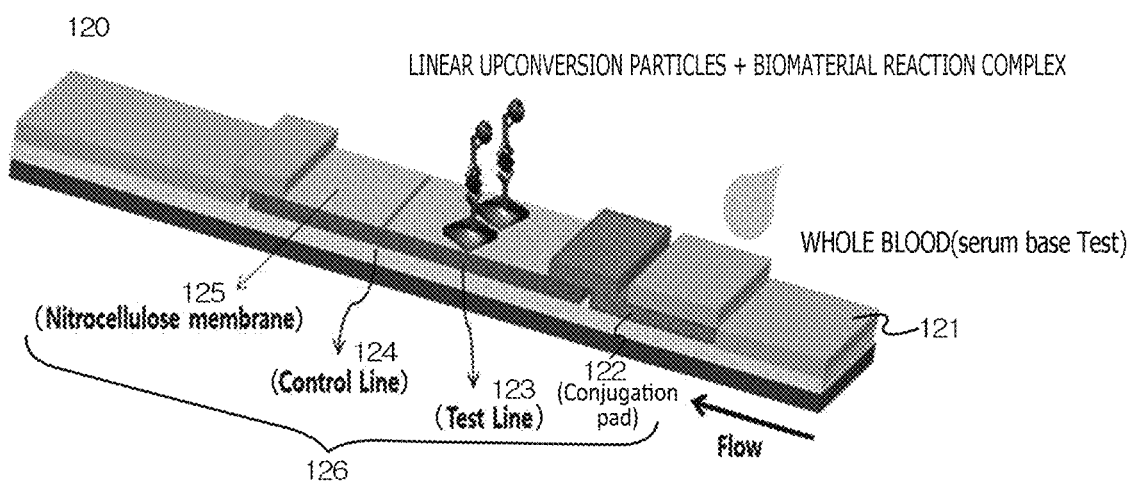

[FIG. 5]
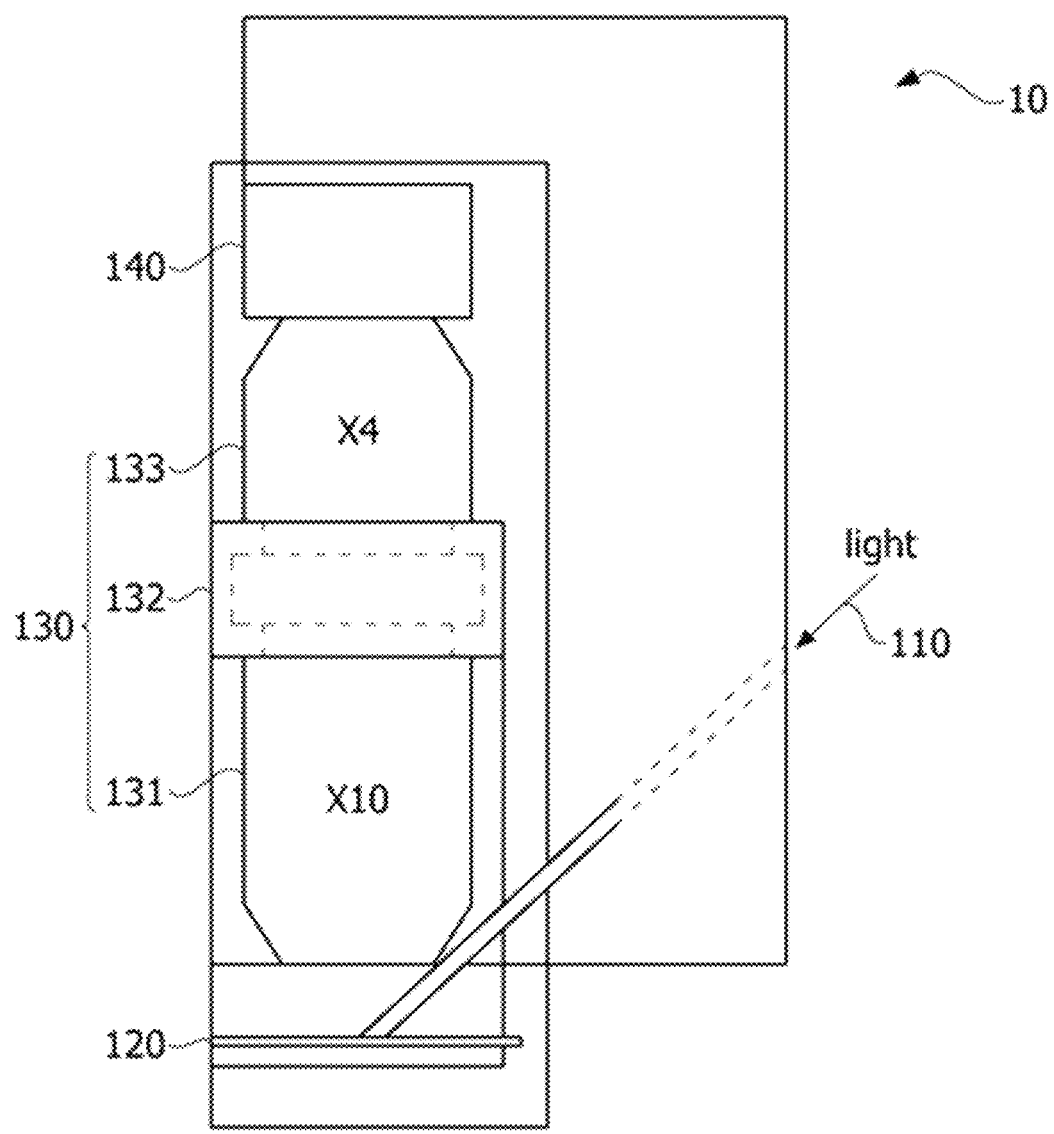

[FIG. 6]
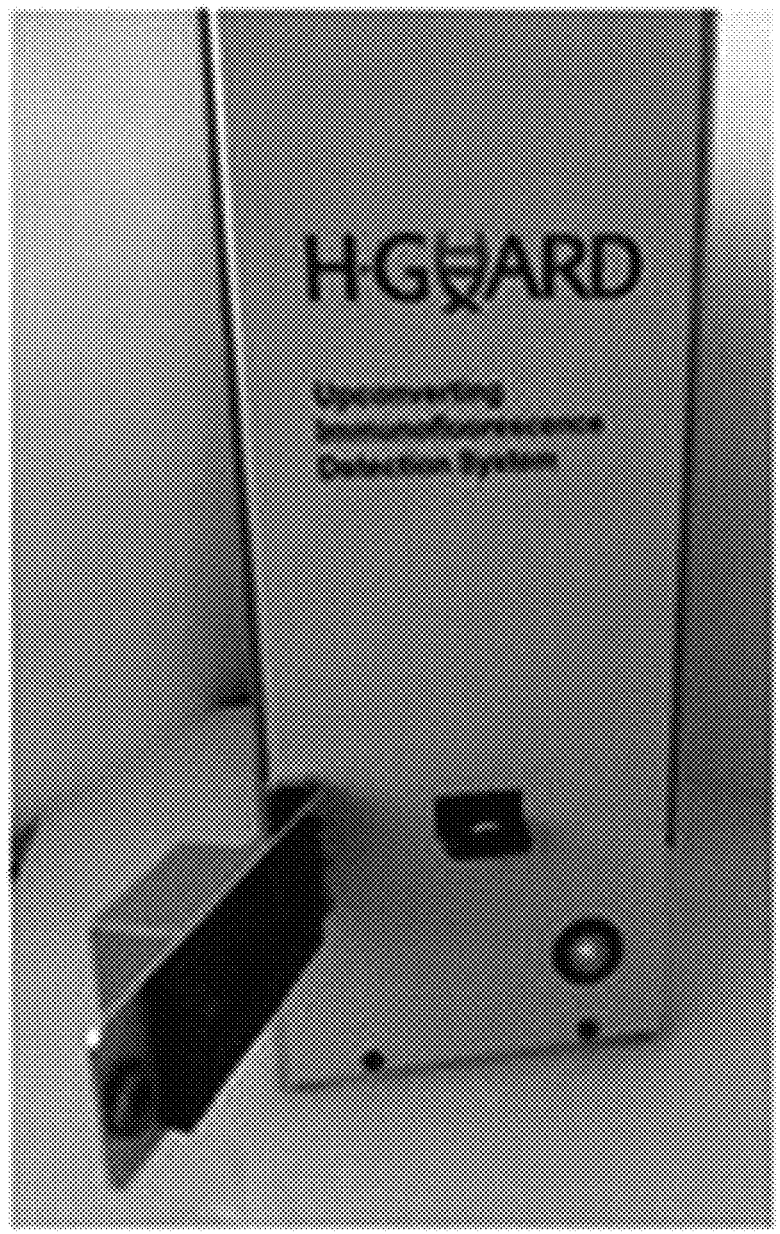

[FIG. 7]
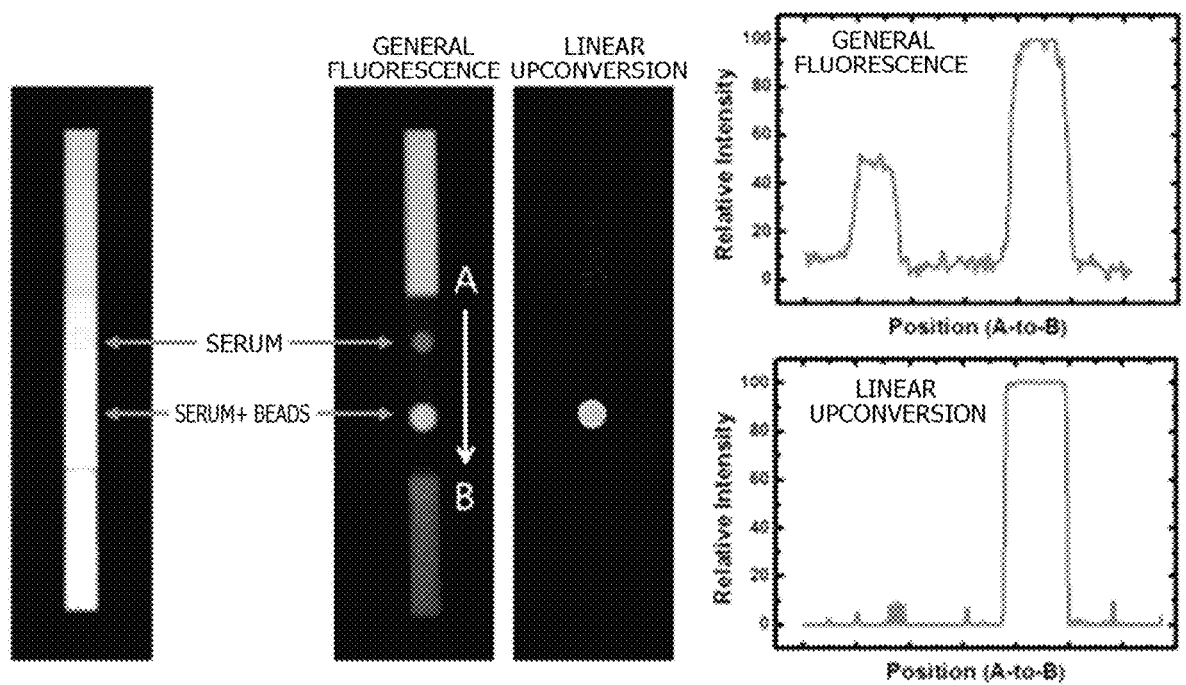
[Fig. 8A]  [Fig. 8B]  [Fig. 8C]  [Fig. 8D]
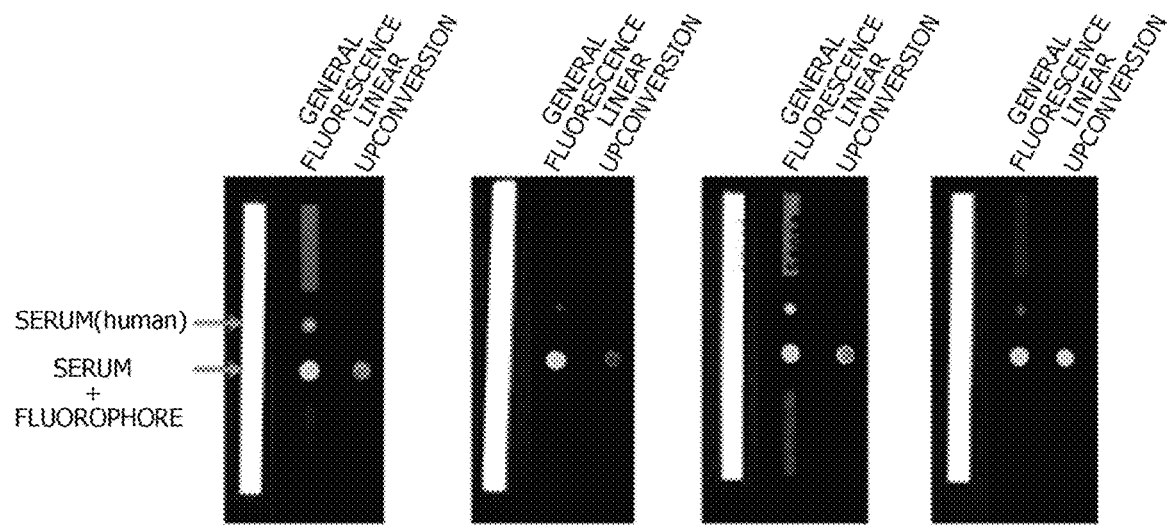

[FIG. 9A]
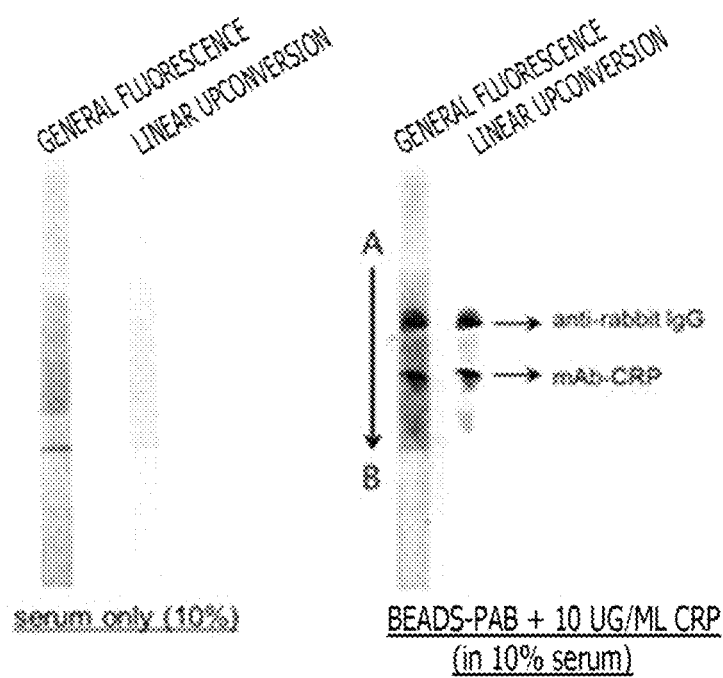
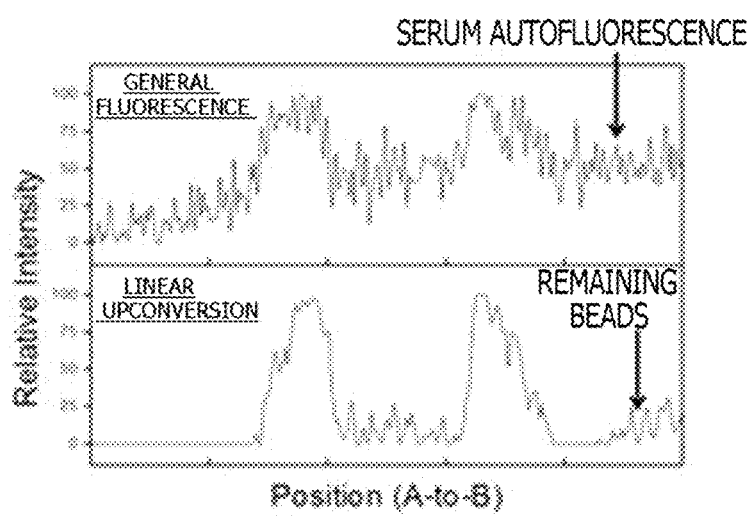
[Fig. 9B]

[FIG. 10]
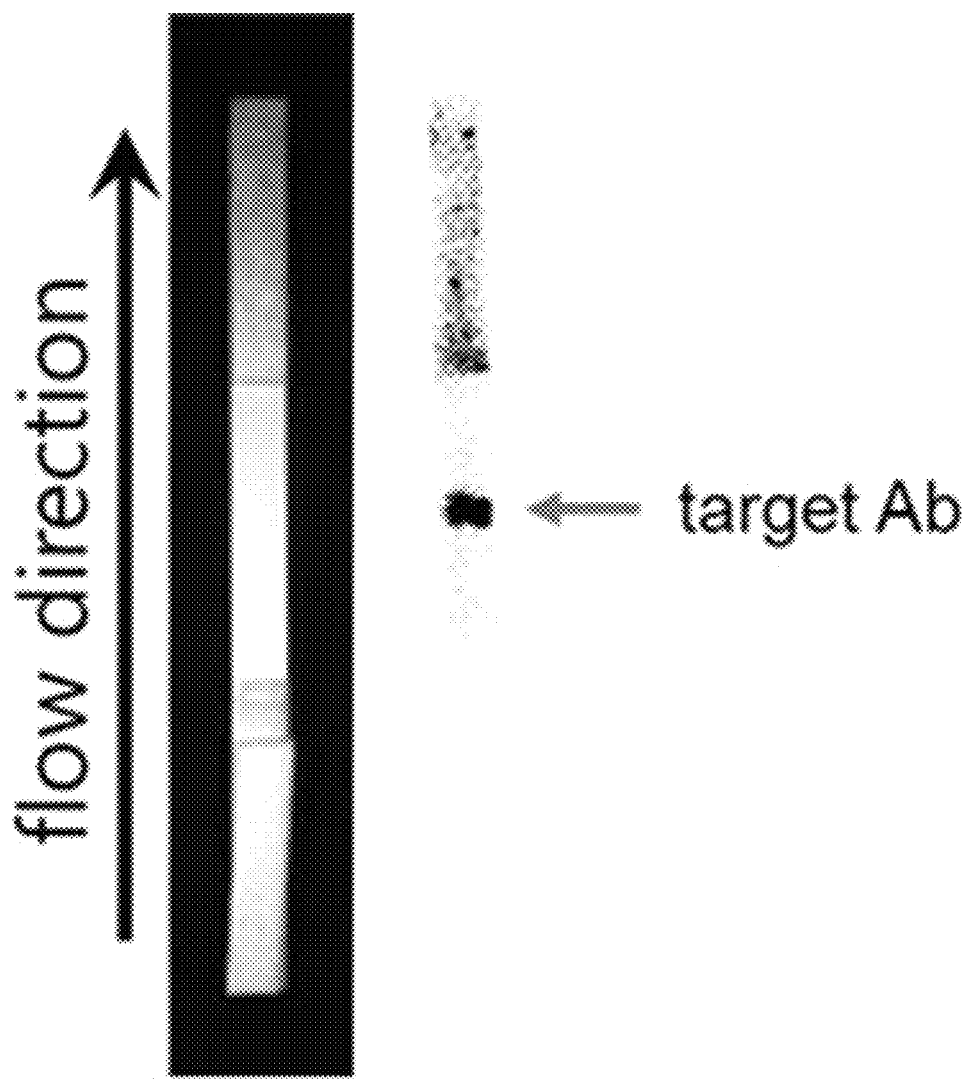

[Fig. 11A]
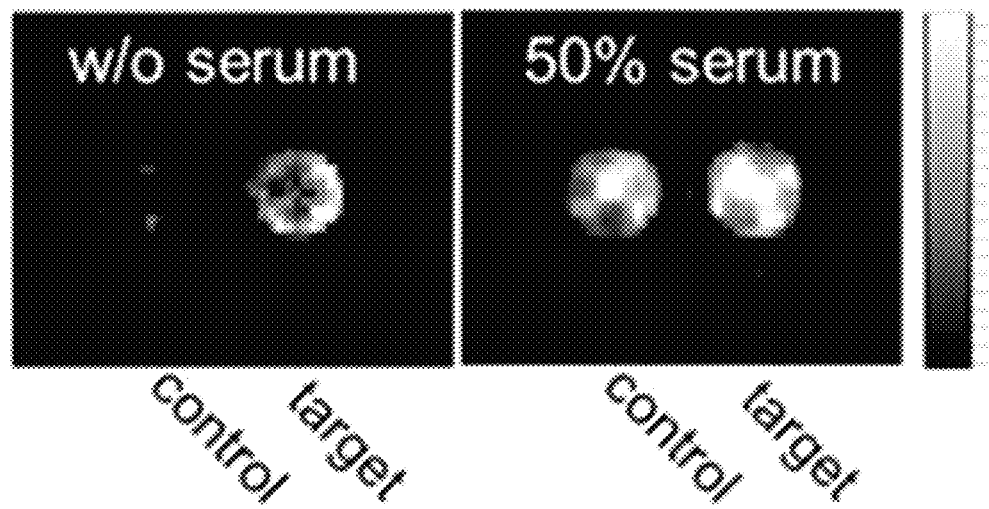
[Fig. 11B]
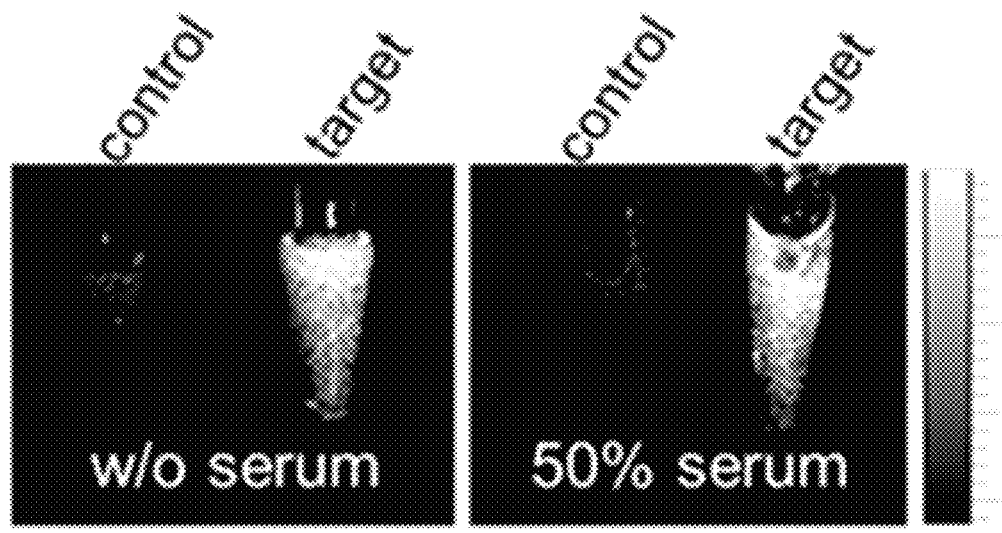

METHOD FOR DETECTING BIOMATERIAL USING LINEAR UPCONVERSION FLUORESCENT PROPERTY

CROSS-REFERENCE TO RELATED APPLICATIONS

This application is a Section 371 of International Application No. PCT/KR2016/005166, filed May 16, 2016, which was published in the Korean language on Nov. 24, 2016, under International Publication No. WO 2016/186412 A1, which claims priority under 35 U.S.C. § 119(b) to Korean Patent Application No. 10-2015-0067872, filed May 15, 2015, and Korean Patent Application No. 10-2016-0059525, filed May 16, 2016, the disclosures of which are incorporated herein by reference in their entirety.

BACKGROUND OF THE INVENTION

The present invention relates to an assay method for detecting a biomaterial using a linear upconversion fluorescent property.

A target specimen (blood, sputum, etc.) or a detection substrate basically has fluorophores, which act as background noise in regards to fluorescence-based detection. In addition, when generally used conventional fluorescent particles are used, such background noise is also detected, and therefore, detection sensitivity of a target signal is limited.

One of the ways to minimize background noise is to utilize upconversion fluorescent materials, instead of general downconversion fluorescence ones, for a signaling label. Conventional upconversion nanoparticles (UCNPs) may have a size-independent maximum emission wavelength and facilitate multiple color emissions by transforming a host crystal and an RE doping material. Taking advantage of such characteristics, UCNPs have been used in flow cytometry, photodynamic therapy, diagnosis, etc., used as fluorescent labels for biological assays such as immunoassays and gene analysis, and also used in chemical detection/cell imaging.

However, in order to detect fluorescence using conventional UCNPs, a non-linear upconversion type of inorganic nanocrystal (absorbs biphotons and multiphotons) was mostly utilized, and a non-linear upconversion type of inorganic nanocrystal is detected with a laser, which is a high-power coherent excitation light source and is expensive, wherein detection is difficult.

For that reason, the inventors developed novel linear UCNPs that can be detected with a conventional LED by applying a linear upconversion fluorescent property to a method for detecting a biomaterial, and thus the present invention was completed.

BRIEF SUMMARY OF THE INVENTION

Disclosure

Technical Problem

The present invention is directed to providing a method for detecting biomaterial by means of a dye having a linear upconversion fluorescent property.

The present invention is also directed to providing a system for detecting a biomaterial by means of a dye having a linear upconversion fluorescent property.

The present invention is also directed to providing a linear upconversion-based kit for diagnosing biomaterial, which includes a fluorophore having a linear upconversion fluorescent property.

Technical Solution

To achieve the above-mentioned objects, the present invention provides a method for detecting a biomaterial by means of a dye having a linear upconversion fluorescent property, the method including:

i) preparing a fluorophore having a linear upconversion fluorescent property;

ii) reacting the fluorophore with the biomaterial to form a reaction complex thereof;

iii) exciting the reaction complex using a light source with a wavelength longer than the maximum emission wavelength of the fluorophore; and iv) detecting and measuring a fluorescence signal with a wavelength shorter than the wavelength of excitation light emitted from the excited reaction complex.

The term "upconversion fluorescence" refers to a wide range of optical phenomena in which high energy light is emitted by absorbing low energy light.

The term "linear upconversion fluorescence" used herein refers to a linear optical phenomenon based on the absorption of single photons, not the absorption of multiple photons. Conventional non-linear upconversion fluorescence is a phenomenon of emitting high energy light by sequentially absorbing two or more photons from fluorescence, and thus has a difference from the linear upconversion of the present invention.

In the detection method of the present invention, there is no limit related to a fluorophore having a linear upconversion fluorescent property, and preferably, a fluorophore having a Stokes' shift of <100 nm. The term "Stokes' shift" refers to the difference in excitation light energy and light emission energy according to Strokes' Law.

In the detection method of the present invention, the fluorophore having a linear upconversion fluorescent property may be, but is not limited to, any one or more selected from the group consisting of a diketo pyrrolo pyrrole (DPP) derivative represented by Formula 1 below, acene, fluorescein, rhodamine, oxazine, thiazine, cyanine, rubrene, borondipyrromethene (BODIPY), resorufin and hemicyanine. However, the fluorophore is not necessarily limited to the above examples, and therefore may be any fluorophore having a linear upconversion fluorescent property, and preferably any fluorophore having a Stokes' shift of <100 nm.

[Formula 1]

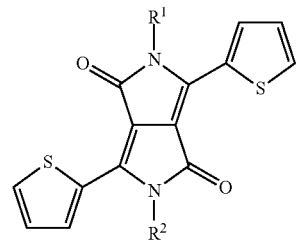

(In Formula 1, $R^1$ and $R^2$ are the same or different, and are hydrogen, a substituted or unsubstituted alkyl group having 1 to 60 carbon atoms, a substituted or unsubstituted cycloalkyl group having 3 to 30 carbon atoms, a substituted or unsubstituted aryl group having 6 to 60 carbon atoms, a substituted or unsubstituted heteroaryl group having 2 to 60 carbon atoms, or a substituted or unsubstituted condensed polycyclic group having 6 to 60 carbon atoms.)

In an exemplary embodiment of the present invention, the DPP derivative may be, but is not limited to, 2,5-bis(2-ethylhexyl)-3,6-di(thiophen-2-yl)pyrrolo[3,4-c]pyrrole-1,4 (2H,5H)-dione [Formula 2];

2,5-bis(2-ethylhexyl)-2,5-dihydro-3,6-diphenyl-pyrrolo[3,4-c]pyrrole-1,4-dione [Formula 3];

5-(2,5-bis(2-ethylhexyl)-1,2,4,5-tetrahydro-1,4-dioxo-3-(thiophen-2-yl)pyrrolo[3,4-c]pyrrol-6-yl)thiophene-2-carbaldehyde [Formula 4]; or 5,5'-(2,5-bis(2-ethylhexyl)-3,6-dioxo-2,3,5,6-tetrahydropyrrolo[3,4-c]pyrrole-1,4-diyl)bis(thiophene-2-carbaldehyde) [Formula 5], and most preferably, 2,5-bis(2-ethylhexyl)-3,6-di(thiophen-2-yl)pyrrolo[3,4-c]pyrrole-1,4 (2H,5H)-dione represented by Formula 2.

[Formula 2]

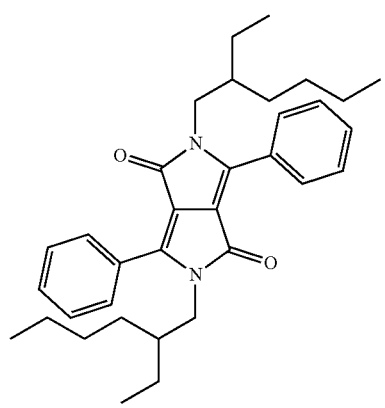

2,5-bis(2-ethylhexyl)-3,6-di(thiophen-2-yl)pyrrolo[3,4-c]pyrrole-1,4(2H,5H)-dione

[Formula 3]

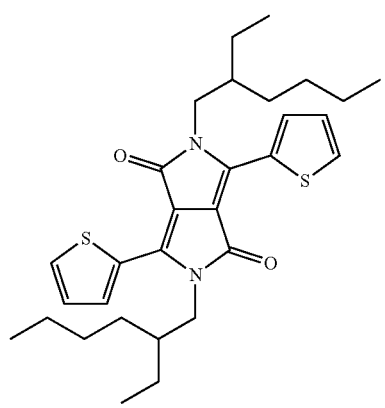

2,5-bis(2-ethylhexyl)-2,5-dihydro-3,6-diphenyl-pyrrolo[3,4-c]pyrrole-1,4-dione

[Formula 4]

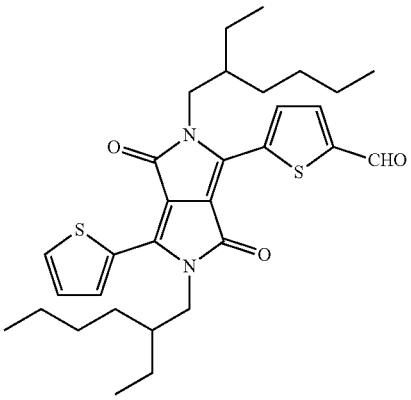

5-(2,5-bis(2-ethylhexyl)-1,2,4,5-tetrahydro-1,4-dioxo-3-(thiophen-2-yl)pyrrolo[3,4-c]pyrrol-6-yl)thiophene-2-carbaldehyde

[Formula 5]

5,5'-(2,5-bis(2-ethylhexyl)-3,6-dioxo-2,3,5,6-tetrahydropyrrolo[3,4-c]pyrrole-1,4-diyl)bis(thiophene-2-carbaldehyde)

In Step i) of the detection method of the present invention, the fluorophore may be directly conjugated to a molecule for detecting a biomaterial. Alternatively, the fluorophore is preferably loaded on or conjugated to a nanostructure, thereby forming a fluorescent nanostructure.

The term "nanostructure" used herein refers to a nanoscale structure, and here, the size of the nanostructure is not limited, and the nanostructure includes particles larger than nanoparticles, that is, microparticles. The nanostructure may have any size suitable for loading or conjugating a fluorescent dye having a linear upconversion fluorescent property of the present invention.

The nanostructure may be, but is not limited to, any one or more selected from the group consisting of nanoparticles, nanobeads, a nanoemulsion, micelles, liposomes and a nanoparticle suspension. In an exemplary embodiment of the present invention, the nanostructure is preferably polystyrene-based beads. In the present invention, the nanobeads may have a size of 1 to 1000 nm, but the size is not limited thereto.

In Step ii) of the detection method of the present invention, the fluorophore may be conjugated to a molecule for detecting a biomaterial, and the molecule for detecting a biomaterial-conjugated fluorophore may react with the biomaterial, thereby forming a reaction complex thereof.

Here, the molecule for detecting a biomaterial may be any one or more selected from the group consisting of a protein, an antibody, a gene, a lipid, an enzyme, an aptamer and a ligand, but the present invention is not limited thereto, and therefore any material capable of complementarily binding to a biomaterial to be detected can be used.

In Step iii) of the detection method of the present invention, the reaction complex may be excited using a light source with a wavelength 5 to 50 nm longer than the maximum emission wavelength of the fluorophore. Here, the light source may be, but is not limited to, a light emitting diode (LED) or a lamp. That is, the light source of the present invention may be any light source other than a laser, and detection can be executed with a conventional LED, which can give a cost reducing effect when utilizing a fluorescence-measuring system of the present invention.

In Step iv) of the detection method of the present invention, an emission signal emitted from the reaction complex may be an emission signal in a wavelength range 10 to 100 nm shorter than a wavelength of the excitation light.

In the detection method of the present invention, the biomaterial may be, but is not limited to, any one selected from the group consisting of a tissue extract, a cell lysate, whole blood, plasma, serum, saliva, ocular humor, cerebrospinal fluid, sweat, urine, milk, ascitic fluid, sinovial fluid, peritoneal fluid and a dried blood spot.

The term "sample" used herein may be any sample capable of being applied to a method or diagnostic kit of the present invention without limitation, and particularly a liquid sample capable of being uniformly applied to a diagnostic kit. In the present invention, an analysis sample may include all substances which can contain a target biomolecule, and particularly, various substances exposed within a living body or isolated from the living body. The substances isolated from the living body include, preferably, blood, urine, nasal mucus, cells, extracted DNA, RNA and a protein.

In addition, the detection method of the present invention may further include manufacturing a biosensor, biochip or kit for detecting a biomaterial by placing the molecule for detecting a biomaterial-conjugated linear upconversion fluorescent nanostructure on a biochip or kit for detecting a biomaterial or a strip sensor.

The present invention also relates to a biomaterial detection system 10, and referring to FIG. 1, the system 10 for detecting a biomaterial by means of a dye having a linear upconversion fluorescent property, which includes a biomaterial diagnostic kit 120 consisting of an injection unit into which a biomaterial is injected, and a reaction unit which includes a fluorophore having a linear upconversion fluorescent property and forms a reaction complex of the biomaterial and the fluorophore;

a light source unit 110 providing a light source to the reaction unit of the biomaterial diagnostic kit;

an emission signal collection unit 130 detecting an emission signal with a wavelength shorter than that of excitation light exciting the fluorophore of the reaction complex; and a measurement unit 140 detecting and measuring the collected emission signal, wherein the light source unit 110 provides a light source with a wavelength longer than the maximum emission wavelength of the fluorophore.

In the detection system, the fluorophore may be a fluorophore having a Stokes' shift of <100 nm, but the present invention is not limited thereto.

Meanwhile, the light source unit may include an excitation filter which filtrates light emitted from the light source, and the emission signal collection unit may include a lens projecting the filtered light. However, the excitation filter is used so that only a predetermined wavelength of the light source is able to penetrate. In addition, the lens of the emission signal collection unit may refer to an objective lens and an eyepiece, and may include an emission filter between the objective lens and the eyepiece like a common microscope. The objective lens is used to concentrate radial light, and the emission filter facilitates the measurement of light concentrated by the objective lens after being delivered to the measurement unit (FIG. 1).

Such a light source unit, the filter and the lens may be arranged at suitable intervals to easily observe the biomaterial.

In addition, in the detection system of the present invention, the diagnostic kit may be a rapid diagnostic kit or ELISA kit, but the present invention is not limited thereto.

Meanwhile, in an exemplary embodiment of the present invention, as the diagnostic kit, a rapid diagnostic kit may be used.

In this case, the rapid diagnostic kit may consist of a sample pad, a conjugate pad, a reaction unit consisting of a signal band and a confirmation band, a membrane and an absorption pad. The sample pad may refer to an injecting unit for injecting a sample, and the conjugate pad and the membrane may refer to the reaction unit.

More specifically, when a biomaterial is added to the sample pad, a liquid sample wets a dried sample pad, and is then transferred to the conjugate pad, and the analyte binds to an antibody stored in a dried state, thereby forming a complex, followed by migration of the complex in the membrane. The signal band and the confirmation band are printed on the surface of the separation membrane, and when the analyte is contained in the sample, the complex may be accumulated in the signal band region. When a certain amount or more of the complex is agglomerated by binding a substance such as gold particles or latex beads to the antibody of the conjugate pad, the complex may be observed as a signal generated from the signal band unit.

In addition, since an antibody binding to the antibody of the storing unit is printed on the confirmation band of the membrane, the absence or presence of the confirmation band is used as a criterion for determining the effectiveness of a test as a result of judging migration of the liquid sample to a part where necessary and action of the antibody, and the absorption pad attached to an end of the separation membrane may serve as pump by absorbing the liquid sample migrated through the separation membrane to allow the liquid sample to continuously migrate.

More specifically, the biomaterial diagnostic kit of the present invention is used to perform a test by storing a fluorophore-chemically linked antibody in the conjugate pad in a dried state as a result of utilizing a linear upconversion fluorescent property, and injecting the sample (biomaterial) into the sample pad. Afterward, an analyte in the sample (biomaterial), which has migrated into the conjugate pad, forms a conjugate with the stored antibody, and then the conjugate moves to the separation membrane. The conjugate is accumulated in the signal band, and a remaining fluorophore-binding antibody is absorbed by the absorption pad through the separation membrane. Here, the conjugate between the analyte selectively adsorbed by the signal band and the fluorophore-linked antibody may produce fluorescence by receiving energy from the light source unit.

In addition, in the detection system, the fluorophore having a linear upconversion fluorescent property may be, but is not limited to, any one or more selected from the group consisting of a diketo pyrrolo pyrrole (DPP) derivative represented by Formula 1 below, acene, fluorescein, rhodamine, oxazine, thiazine, cyanine, rubrene, boron-dipyrromethene (BODIPY), resorufin and hemicyanine, and may be any fluorophore having a linear upconversion fluorescent property, and preferably any fluorophore having a Stokes' shift of <100 nm.

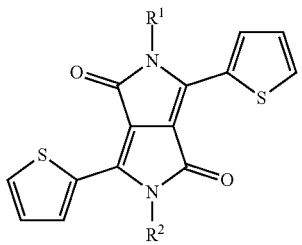

[Formula 1]

(In Formula 1, $R^1$ and $R^2$ are the same or different, and are hydrogen, a substituted or unsubstituted alkyl group having 1 to 60 carbon atoms, a substituted or unsubstituted cycloalkyl group having 3 to 30 carbon atoms, a substituted or unsubstituted aryl group having 6 to 60 carbon atoms, a substituted or unsubstituted heteroaryl group having 2 to 60 carbon atoms, or a substituted or unsubstituted condensed polycyclic group having 6 to 60 carbon atoms.)

In an exemplary embodiment of the present invention, the DPP derivative may be, but is not limited to, 2,5-bis(2-ethylhexyl)-3,6-di(thiophen-2-yl)pyrrolo[3,4-c]pyrrole-1,4 (2H,5H)-dione; 2,5-bis(2-ethylhexyl)-2,5-dihydro-3,6-diphenyl-pyrrolo[3,4-c]pyrrole-1,4-dione; 5-(2,5-bis(2-ethylhexyl)-1,2,4,5-tetrahydro-1,4-dioxo-3-(thiophen-2-yl) pyrrolo[3,4-c]pyrrol-6-yl)thiophene-2-carbaldehyde; or 5,5'-(2,5-bis(2-ethylhexyl)-3,6-dioxo-2,3,5,6-tetrahydropyrrolo[3,4-c]pyrrole-1,4-diyl)bis(thiophene-2-carbaldehyde), and most preferably, 2,5-bis(2-ethylhexyl)-3,6-di(thiophen-2-yl)pyrrolo[3,4-c]pyrrole-1,4(2H,5H)-dione represented by Formula 2.

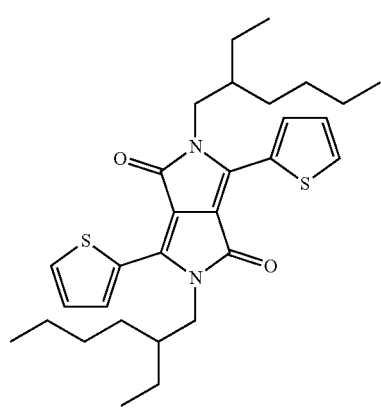

[Formula 2]

2,5-bis(2-ethylhexyl)-3,6-di(thiophen-2-yl)pyrrolo[3,4-c]pyrrole-1,4(2H,5H)-dione

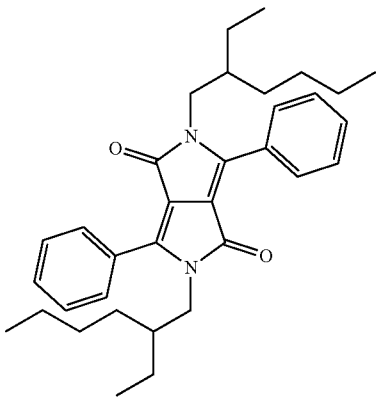

[Formula 3]

2,5-bis(2-ethylhexyl)-2,5-dihydro-3,6-diphenyl-pyrrolo[3,4-c]pyrrole-1,4-dione

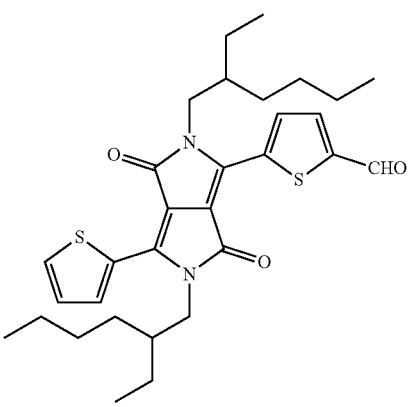

[Formula 4]

5-(2,5-bis(2-ethylhexyl)-1,2,4,5-tetrahydro-1,4-dioxo-3-(thiophen-2-yl)pyrrolo[3,4-c]pyrrol-6-yl)thiophene-2-carbaldehyde

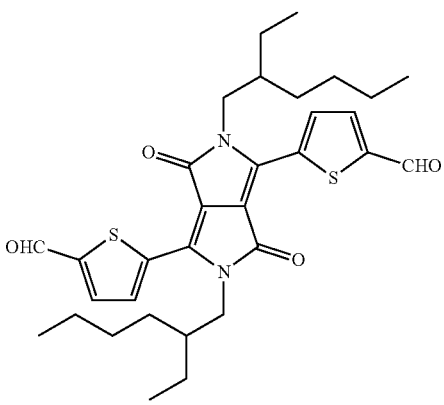

[Formula 5]

5,5'-(2,5-bis(2-ethylhexyl)-3,6-dioxo-2,3,5,6-tetrahydropyrrolo[3,4-c]pyrrole-1,4-diyl)bis(thiophene-2-carbaldehyde)

In the detection system of the present invention, the fluorophore may be directly conjugated to a molecule for detecting a biomaterial. In addition, the fluorophore may be loaded on or conjugated to a nanostructure, thereby forming a fluorescent nanostructure.

The nanostructure may be, but is not limited to, any one selected from the group consisting of nanoparticles, nanobeads, a nanoemulsion, micelles, liposomes and a nanoparticle suspension. In an exemplary embodiment of the present invention, the nanostructure is preferably polystyrene-based beads. In the present invention, the nanobeads may have a size of 1 to 1000 nm, but the size is not limited thereto.

The reaction complex of the biomaterial and the fluorophore of the detection system may be formed by conjugating the fluorophore to the molecule for detecting a biomaterial in the reaction unit, and reacting the molecule for detecting a biomaterial-conjugated fluorophore with the biomaterial, but the present invention is not limited thereto.

In the detection system, the molecule for detecting a biomaterial may be any one or more selected from the group consisting of a protein, an antibody, a gene, a lipid, an enzyme, an aptamer and a ligand, but the present invention is not limited thereto, and therefore any material capable of complementarily binding to a biomaterial to be detected can be used.

In the detection system, the light source with a wavelength longer than the maximum emission wavelength of the fluorophore may be, but is not limited to, a light source with a wavelength 5 to 50 nm longer than the maximum emission wavelength of the fluorophore. Here, the light source may be, but is not limited to, a light emitting diode (LED) or a lamp. That is, the light source of the present invention may be any light source other than a laser, and detection can be executed with a conventional LED, which can give a cost reducing effect when utilizing a fluorescence-measuring system of the present invention.

In the detection system, the emission signal of the fluorophore may be an emission signal with a wavelength shorter than a wavelength of the excitation light, and may be an emission signal in a wavelength range 10 to 100 nm shorter than a wavelength of the excitation light.

In the detection system, the biomaterial may be, but is not limited to, any one selected from the group consisting of a tissue extract, a cell lysate, whole blood, plasma, serum, saliva, ocular humor, cerebrospinal fluid, sweat, urine, milk, ascitic fluid, sinovial fluid, peritoneal fluid and a dried blood spot.

In addition, the present invention provides a linear upconversion-based biomaterial diagnostic kit, which includes a fluorophore having a linear upconversion fluorescent property.

The term "diagnostic kit" used herein may include the linear upconversion fluorescent nanoparticles of the present invention and a biomaterial-detecting molecule, and further include other reagents, tools, etc., necessary for a process of detecting a target biomaterial. In addition, the diagnostic kit may be manufactured as a rapid diagnostic kit capable of detecting the biomaterial of the present invention, or may be manufactured as other various types of diagnostic kits.

The biomaterial-detecting molecule may be any one or more selected from the group consisting of a protein, an antibody, a gene, a lipid, an enzyme, an aptamer and a ligand, but the present invention is not limited thereto, and most preferably an antibody.

The term "biomaterial" used herein refers to a material that can be found inside or outside of a living body, and includes all materials generating a specific reaction in the living body, creating a specific response in the living body or produced by a specific state or reaction. Preferably, the biomaterial of the present invention is a compound, a protein, DNA, RNA or cells. The term "target biomaterial" used herein refers to a target substance of interest of which the presence or content is detected using the diagnostic kit of the present invention, and specifically, a substance that specifically interacts with a detection molecule constituting the diagnostic kit.

The linear upconversion fluorescent nanostructure may be prepared by loading or conjugating a fluorescent dye having a linear upconversion fluorescent property on or to a nanostructure.

The fluorescent dye having a linear upconversion fluorescent property may be any one or more selected from the group consisting of a diketo pyrrolo pyrrole (DPP) derivative represented by Formula 1 below, acene, fluorescein, rhodamine, oxazine, thiazine, cyanine, rubrene, borondipyrromethene (BODIPY), resorufin and hemicyanine.

[Formula 1]

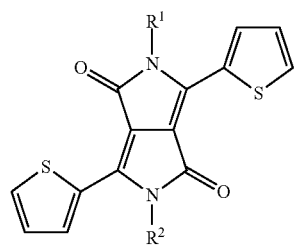

(In Formula 1, $R^1$ and $R^2$ are the same or different, and are hydrogen, a substituted or unsubstituted alkyl group having 1 to 60 carbon atoms, a substituted or unsubstituted cycloalkyl group having 3 to 30 carbon atoms, a substituted or unsubstituted aryl group having 6 to 60 carbon atoms, a substituted or unsubstituted heteroaryl group having 2 to 60 carbon atoms, or a substituted or unsubstituted condensed polycyclic group having 6 to 60 carbon atoms.)

In order to observe fluorescence using conventional UCNPs, a non-linear upconversion type of inorganic nanocrystal (absorbs biphotons and multiphotons) was mostly utilized, and the non-linear upconversion type of inorganic nanocrystal is observed with a laser, which is a high-power coherent excitation light source and is expensive, wherein observation is difficult. However, the linear upconversion fluorescent nanoparticle-based diagnostic kit of the present invention can be observed with a LED, which can give a cost reducing effect.

In an exemplary embodiment of the present invention, 3,6-di(thiophen-2-yl)pyrrolo[3,4-c]pyrrole-1,4(2H,5H)-dione was synthesized using thiophene-2 carbonitrile and dimethyl succinate, and then ethylhexyl bromide was added, thereby synthesizing 2,5-bis(2-ethylhexyl)-3,6-di(thiophen-2-yl)pyrrolo[3,4-c]pyrrole-1,4(2H,5H)-dione. Afterward, 2,5-bis(2-ethylhexyl)-3,6-di(thiophen-2-yl)pyrrolo[3,4-c]pyrrole-1,4(2H,5H)-dione was loaded on polystyrene beads to synthesize novel linear UCNPs, and it has been confirmed that the developed particles exhibit an upconversion fluorescent property. In addition, a diagnostic system for a rapid kit was developed by means of the novel linear UCNPs of the present invention.

Unless defined otherwise, all the technical and scientific terms used in the specification have the same meanings as conventionally understood by those of ordinary skill in the art to which the present invention belongs. Generally, the nomenclature used herein is well known in the art and conventionally used.

Advantageous Effects

The linear upconversion fluorescent nanostructure of the present invention can detect only signals of particles without background noise, thereby dramatically enhancing an S/N ratio and sensitivity. In addition, since fluorescence of the linear upconversion nanostructure of the present invention can be observed even with a conventional LED, a cost reducing effect can be imparted when utilizing a fluorescence-measuring system of the present invention.

BRIEF DESCRIPTION OF THE SEVERAL VIEWS OF THE DRAWINGS

The foregoing summary, as well as the following detailed description of the invention, will be better understood when read in conjunction with the appended drawings. For the purpose of illustrating the invention, there are shown in the drawings embodiments which are presently preferred. It should be understood, however, that the invention is not limited to the precise arrangements and instrumentalities shown.

In the drawings:

FIG. 1 is a block diagram of a biomaterial detection system of the present invention;

FIG. 2A shows absorption and fluorescence spectra of DPP-Th of the present invention and FIG. 2B shows linear upconversion fluorescence spectra of DPP-Th-loaded polystyrene nanobeads (DPP-Th: 2,5-bis(2-ethylhexyl)-3,6-di(thiophen-2-yl)pyrrolo[3,4-c]pyrrole-1,4(2H,5H)-dione);

FIG. 3 shows a linear upconversion fluorescent property based on the concentration of a loaded fluorophore of DPP-Th-loaded polystyrene nanobeads of the present invention (DPP-Th: 2,5-bis(2-ethylhexyl)-3,6-di(thiophen-2-yl)pyrrolo[3,4-c]pyrrole-1,4(2H,5H)-dione);

FIG. 4 is a schematic diagram of a rapid kit for diagnosing a biomaterial prepared by means of a linear upconversion fluorophore of the present invention;

FIG. 5 is a schematic diagram illustrating the configuration of a detection system for the linear upconversion fluorescence-based rapid kit of the present invention;

FIG. 6 shows a measurement system for the rapid kit capable of detecting a biomaterial by means of linear UCNPs according to the present invention;

FIG. 7 shows the sensitivity of DPP-Th-loaded nanobeads towards a linear upconversion fluorescence signal, compared with a general downconversion fluorescence signal, on a diagnostic strip of the rapid kit of the present invention;

FIGS. 8A, 8B, 8C, and 8D show the results of comparing the sensitivity of linear upconversion fluorescence signal with the sensitivity of downconversion fluorescence signal of DPP-Th-loaded nanobeads (FIG. 8A), rubrene-loaded polymer surfactant micelle nanoparticles (micelle, Pluronic F127) (FIG. 8B), a resorufin solution (FIG. 8C) and a rhodamine B solution (FIG. 8D), based on human serum, on a diagnostic strip of the rapid kit of the present invention;

FIGS. 9A and 9B show the results of identifying immune responses on a rapid kit-based membrane by means of linear UCNPs according to the present invention;

FIG. 10 shows the result of application of a rapid diagnostic kit by means of linear UCNPs according to the present invention; and FIGS. 11A and 11B show the result of gene analysis by utilizing a linear upconversion fluorescent property according to the present invention.

DETAILED DESCRIPTION OF THE INVENTION

Modes of the Invention

Hereinafter, the present application will be described in further detail with reference to examples. The examples are merely provided to more fully describe the present application, and it will be obvious to those of ordinary skill in the art that the scope of the present application is not limited to the following examples.

Example 1. Synthesis of Linear Upconversion Dye (DPP-Th)

Example 1-1. Synthesis of 3,6-di(thiophen-2-yl)pyrrolo[3,4-c]pyrrole-1,4(2H,5H)-dione A mixture of sodium (2.65 g, 0.13 mol) and $FeCl_3$ was dissolved in t-amyl alcohol (250 mL). The mixture was stirred at 110° C. until it became light yellow. After heating for 3 hours at 110° C., thiophene-2 carbonitrile (11.9 g, 0.12 mol) was added to the reaction mixture which was then maintained for 0.5 hour. After slowly adding dimethyl succinate (5.29 g, 0.04 mol) drop-wise for 1.5 hours, the reaction mixture was stirred at 120° C. for 4 hours. Subsequently, following cooling to 0° C., the reaction mixture was precipitated with MeOH/HCl. A solid obtained thereby was purified, washed with hot MeOH, and dried under vacuum. Thus, 10.2 g of dark red solid 3,6-di(thiophen-2-yl)pyrrolo[3,4-c]pyrrole-1,4(2H,5H)-dione (84.8%) was obtained, and used without purification.

Example 1-2. Synthesis of 2,5-bis(2-ethylhexyl)-3,6-di(thiophen-2-yl)pyrrolo[3,4-c]pyrrole-1,4(2H,5H)-dione (DPP-Th)

The 3,6-di(thiophen-2-yl)pyrrolo[3,4-c]pyrrole-1,4(2H,5H)-dione (4 g, 0.013 mol) obtained in Example 1-1 and $K_2CO_3$ (5.5 g, 0.039 mol) were suspended in DMF (140 mL) under an argon atmosphere. The reaction mixture was stirred at 110° C. for 3 hours. After adding 2-ethylhexyl bromide (9 g, 0.046 mol) drop-wise, the reaction mixture was maintained for 24 hours. After cooling at room temperature, a solvent was removed using a rotary evaporator. Subsequently, water was added to purify a crude product. A residue was recrystallized with MeOH and purified. Finally, 1.1 g of brown solid 2,5-bis(2-ethylhexyl)-3,6-di(thiophen-2-yl)pyrrolo[3,4-c]pyrrole-1,4(2H,5H)-dione (15.7%) was obtained.

Example 2. Preparation of Linear Upconversion Nanobeads and Fluorescent Characteristic of Linear Upconversion Nanobeads 100 μl of a tetrahydrofuran (THF) solution containing $5 \times 10^{-5}$ M DPP-Th obtained in Example 1 was added to 600 μl of 0.4 w/v % carboxylated polystyrene beads (100 nm, Invitrogen). A mixture solution was slowly stirred at room temperature for 30 minutes. Afterward, THF was removed with a rotary evaporator, resulting in linear upconversion nanobeads.

In addition, FIG. 2A shows absorption and fluorescence spectra of DPP-Th of the present invention and FIG. 2B shows linear upconversion fluorescence spectra of DPP-Th-loaded polystyrene nanobeads (DPP-Th: 2,5-bis(2-ethylhexyl)-3,6-di(thiophen-2-yl)pyrrolo[3,4-c]pyrrole-1,4(2H, 5H)-dione). It can be confirmed that the fluorophore has a Stokes' shift of approximately 20 nm, and the loaded polystyrene nanobeads have a fluorescent component in a wavelength range (540-570 nm) shorter than that of excitation light under excitation at 580 nm.

Specifically, a fluorescent property of the novel linear upconversion nanostructure was confirmed. As a result, it was confirmed that the developed particles have an upconversion fluorescent component emitting shorter wavelength light as a result of absorbing longer wavelength light. In addition, fluorescence intensity based on the concentration of the loaded fluorescent dye was measured. The results are shown in FIG. 3.

Example 3. Development of Linear UCNP-Based Rapid Diagnostic Kit and Measurement System A rapid kit for diagnosing a biomaterial by means of the linear UCNPs of Example 2 was developed (FIG. 4).

The rapid kit 120 was manufactured based on a generally known configuration. Specifically, a rapid diagnostic kit 120 including a sample pad 121, a conjugation pad 122, a membrane 125 and an absorption pad was manufactured.

Meanwhile, the sample pad of the rapid diagnostic kit 120 refers to an injection unit 121 of the present invention, and the conjugation pad 122, a signal pad 123, a confirmation band 124, the membrane 125 and an absorption pad refer to a reaction unit 126.

In addition, a biomaterial detection system 10 shown in FIG. 5 was constructed by means of the linear UCNP-based rapid diagnostic kit 120. Specifically, a LED 110 was disposed such that excitation light was applied to the rapid diagnostic kit 120 through an excitation filter (not shown), and fluorescence generated from the diagnostic kit 120 was disposed so as to reach a measurement unit 140 through an objective lens 131, an emission filter 132 and an eyepiece 133. The objective lens 131 was arranged to adjust a focal distance on the kit 120, and designed to measure a fluorescence signal in a corresponding focal region on the kit 120 (FIGS. 5 and 6).

Example 4. Test for Fluorescent Signal Sensitivity of Linear Upconversion Nanobeads on a Serum Sample Linear upconversion fluorescence signal sensitivity was measured by means of the linear UCNPs of Example 2, compared to serum (background), on a diagnostic strip (FIG. 7). First, 1 µl of fetal bovine serum (FBS) and DPP-Th nanobeads (4 mg/ml in DW) diluted in FBS at 1/10 were placed on diagnostic strips, respectively. Afterward, a linear upconversion fluorescent property was confirmed using an imaging system according to the conditions shown in Table 1 below. Linear upconversion fluorescent and general fluorescent properties mentioned herein are measured under the conditions in Table 1 below.

TABLE 1

Conditions for measuring linear upconversion fluorescence and general downconversion fluorescence

|  | General fluorescence (downconversion) | Linear upconversion fluorescence |
|---|---|---|
| Wavelength of excitation light | 500 nm | 590 nm |
| Measured emission wavelength | 585 nm | 550 nm |

Referring to FIG. 7, it can be seen that a target signal with high sensitivity without background noise was measured using a light source such as an LED by utilizing a linear upconversion fluorescent property according to the present invention.

Example 5. Test for Fluorescence Signal Sensitivity of Linear Upconversion Fluorophore on a Serum Sample Linear upconversion fluorescence signal sensitivity and downconversion fluorescence signal sensitivity of the DPP-Th-loaded nanobeads of Example 2, rubrene-loaded polymer surfactant micelle nanoparticles (micelle; Pluronic F127), a resorufin aqueous solution, and a rhodamine B aqueous solution were compared based on a serum sample. The rubrene-loaded micelle nanoparticles were prepared by drying 20 mg of a polymer surfactant (Pluronic F127) and 1 mg of rubrene in a THF solution, and adding distilled water for reconstitution (diluted to the final rubrene concentration of $4 \times 10^{-4}$M). The resorufin aqueous solution and the rhodamine B aqueous solution were prepared in a phosphate-buffered solution (PBS, pH 8.0) with distilled water at a concentration of $10^{-5}$M, respectively, and DPP-Th was prepared by being diluted with a dye concentration of $10^{-5}$ M. The materials were mixed with human serum at a volume ratio of 1:1 and placed on diagnostic strips to identify linear upconversion fluorescent properties (FIGS. 8A-8D). As shown in FIGS. 8A-8D, it was identified that the linear upconversion fluorescence according to the present invention has almost no background noise caused by the auto-fluorescence of serum as compared to general fluorescence.

Example 6. Confirmation of Immune Response Using Linear UCNPs

A surface of the linear UCNPs of Example 2 was modified with antibodies, and immune response tests were carried out using serum and protein solutions on a nitrocellulose membrane. The antibody modification process is as follows: an 1-ethyl-3-(3-dimethylaminopropyl)carbodiimide hydrochloride aqueous solution (30 µl, 100 mg/ml) was added to an aqueous solution containing the linear UCNPs of Example 2 (1 ml, 3 mg/ml), and the resulting mixture was reacted at room temperature for 15 minutes. Here, an anti C-reactive protein (CRP) polyclonal antibody (pAb-CRP; Millipore, Calbiochem) was added (15 µl, 10 mg/ml) and reacted at room temperature for 90 minutes. The resulting product was centrifuged at 12,000 rpm for 15 minutes, washed three times, and blocked with 3% bovine serum albumin (BSA).

An experiment for confirming an immune response was performed on a nitrocellulose membrane as follows. A membrane to which a control antibody (antirabbit IgG; R&D Systems) and a test antibody (mAb-CRP; R&D system) were fixed was blocked with a blocking buffer (1% BSA-containing PBS), and washed with PBS three times. Afterward, a solution in which the antibody-modified linear UCNPs, an antigen (CRP) and serum were mixed was applied to an entire surface of the membrane, and then washed with PBST three times. Following the immune response experiment, fluorescence of the nitrocellulose membrane was measured, and the results are shown in FIGS. 9A and 9B. As shown in FIG. 9A, adsorption of serum itself to the entire surface of the membrane after PBST washing can be confirmed by means of general fluorescence. It can be seen that, when the mixture of the antigen, the antibody-modified linear UCNPs and the serum was applied, strong fluorescence was selectively emitted from the control and the test antibody-fixed region. From the general fluorescence, a fluorescence signal based on the adsorption of the serum contained in the solution applied by the membrane was also detected, and it acted as strong background noise, and therefore it can be seen that a signal of nanoparticles binding to the antibody-fixed region is measured with high sensitivity in the linear upconversion fluorescence.

Example 7. Application of Linear UCNP-Based Rapid Diagnostic Kit

The antibody-modified linear UCNPs of Example 6 were loaded onto the conjugation pad of the diagnostic kit according to Example 3, and then a particle flow property caused by eluent loading was observed with a linear upconversion signal. The result is shown in FIG. 10. As shown in FIG. 10, the particle flow property was identified in a linear upconversion fluorescence mode, and a signal representing minimal background noise in the membrane region can be observed.

Example 8. Linear Upconversion Fluorescence-Based Gene Analysis

The linear upconversion fluorescent property was applied to gene analysis. A method for detecting a target gene by means of probe gene-conjugated metal nanoparticles has been well-known. In this example, a linear upconversion fluorescence technique according to the present invention was applied to the conventionally known method. Specifically, a gold nanoparticle-fluorophore platform (gold nanobeacon) may be manufactured to be utilized as a turn-on fluorescent sensor through target DNA hybridization. Gene sequences used in the gene analysis are as follows:

```
Probe DNA sequence (hairpin type):
5'-SH-(CH2)6-TCG CTG AGA TCG GGA TCC CCA AAA TCA
GCG A-(CH2)6-TAMRA-3' (Bioneer)

Target DNA sequence:
5'-GGG GAT CCC GAT CTC AG-3' (Bioneer)
```

15 nm Au NP and probe DNA were reacted at a molar ratio of 1:100. Then, a NaCl solution (5 M) was added to the reaction product at one-hour intervals a total of four times to adjust the final NaCl concentration to 0.3 M. In addition, the resulting product was purified through three cycles of centrifugation (14,000 rpm, 30 min, 4° C.).

The probe DNA-conjugated gold nanoparticles were reacted with target DNA, and then fluorescence was measured. Specifically, 1.5 nM nanobeacon was reacted with 100 nM target DNA (pH 7 Tris buffer) at 37° C. for 1 hour, and generated fluorescence signals were compared depending on the absence or presence of serum. The result is shown in FIGS. 11A-11B.

Referring to FIGS. 11A and 11B, fluorescence of an extinct fluorophore (TAMRA) dequenched by the target DNA can be observed in a serum-free environment. It is observed in a general fluorescence mode, and the fluorescence signal generated by the target DNA is hidden by the autofluorescence of the serum in a serum-present environment (50% volume ratio). However, it can be seen that the fluorescence signal generated from the fluorophore can be clearly observed regardless of the absence or presence of serum in a linear upconversion fluorescence mode.

EXPLANATION OF REFERENCE NUMERALS

10: Biomaterial detection system
110: Light source unit
120: Diagnostic kit
121: Injection unit
122: Conjugate pad
123: Signal band
124: Confirmation band
125: Membrane
126: Reaction unit
130: Generated signal collection unit
131: Objective lens
132: Emission filter
133: Eyepiece
140: Measurement unit It will be appreciated by those skilled in the art that changes could be made to the embodiments described above without departing from the broad inventive concept thereof. It is understood, therefore, that this invention is not limited to the particular embodiments disclosed, but it is intended to cover modifications within the spirit and scope of the present invention as defined by the appended claims.

The invention claimed is:

1. A method for detecting a biomaterial by means of a dye having a linear upconversion fluorescent property, the method comprising:
   i) preparing a fluorophore having a linear upconversion fluorescent property;
   ii) reacting the fluorophore with the biomaterial to form a reaction complex thereof;
   iii) exciting the reaction complex using a light source with a wavelength longer than the maximum emission wavelength of the fluorophore; and
   iv) detecting and measuring a fluorescence signal with a wavelength shorter than the wavelength of excitation light emitted from the excited reaction complex;
   wherein the fluorophore has a Stokes' shift of <100 nm,
   in Step i), the fluorophore is loaded on or conjugated to a nanostructure, thereby forming a fluorescent nanostructure,
   in Step iii), the reaction complex is excited using a light source with a wavelength 5 to 50 nm longer than the maximum emission wavelength of the fluorophore, and
   in Step iv), the emission signal emitted from the reaction complex is an emission signal in a wavelength range 10 to 100 nm shorter than that of the excitation light.

2. The method of claim 1, wherein the fluorophore having a linear upconversion fluorescent property is any one or more selected from the group consisting of a diketo pyrrolo pyrrole (DPP) derivative represented by Formula 1 below, acene, fluorescein, rhodamine, oxazine, thiazine, cyanine, rubrene, boron-dipyrromethene (BODIPY), resorufin and hemicyanine:

[Formula 1]

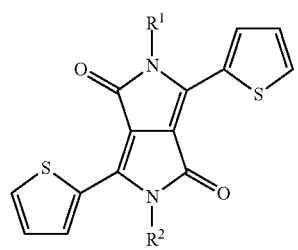

where $R^1$ and $R^2$ are the same or different, and are hydrogen, a substituted or unsubstituted alkyl group having 1 to 60 carbon atoms, a substituted or unsubstituted cycloalkyl group having 3 to 30 carbon atoms, a substituted or unsubstituted aryl group having 6 to 60 carbon atoms, a substituted or unsubstituted heteroaryl group having 2 to 60 carbon atoms, or a substituted or unsubstituted condensed polycyclic group having 6 to 60 carbon atoms.

3. The method of claim 2, wherein the DPP derivative is 2,5-bis(2-ethylhexyl)-3,6-di(thiophen-2-yl)pyrrolo[3,4-c]pyrrole-1,4(2H,5H)-dione;

2,5-bis(2-ethylhexyl)-2,5-dihydro-3,6-diphenyl-pyrrolo[3,4-c]pyrrole-1,4-dione;

5-(2,5-bis(2-ethylhexyl)-1,2,4,5-tetrahydro-1,4-dioxo-3-(thiophen-2-yl)pyrrolo[3,4-c]pyrrol-6-yl)thiophene-2-carbaldehyde; or 5,5'-(2,5-bis(2-ethylhexyl)-3,6-dioxo-2,3,5,6-tetrahydropyrrolo[3,4-c]pyrrole-1,4-diyl)bis(thiophene-2-carbaldehyde).

4. The method of claim 1, wherein the nanostructure is any one or more selected from the group consisting of nanoparticles, nanobeads, a nanoemulsion, micelles, liposomes and a nanoparticle suspension.

5. The method of claim 1, wherein, in Step ii), the fluorophore is conjugated to a molecule for detecting a biomaterial, and the molecule for detecting a biomaterial-conjugated fluorophore may react with the biomaterial, thereby forming a reaction complex thereof.

6. The method of claim 5, wherein the molecule for detecting a biomaterial is any one or more selected from the group consisting of a protein, an antibody, a gene, a lipid, an enzyme, an aptamer and a ligand.

7. The method of claim 1, wherein the light source in Step iii) is a laser, a light emitting diode (LED) or a lamp.

8. The method of claim 1, wherein the biomaterial is selected from the group consisting of a tissue extract, a cell lysate, whole blood, plasma, serum, saliva, ocular humor, cerebrospinal fluid, sweat, urine, milk, ascitic fluid, sinovial fluid, peritoneal fluid and a dried blood spot.

* * * * *